US006245953B1

(12) United States Patent
Yamaguchi et al.

(10) Patent No.: US 6,245,953 B1
(45) Date of Patent: Jun. 12, 2001

(54) METHOD FOR RECOVERING FLUORINE-CONTAINING SOLVENTS

(75) Inventors: Fumihiko Yamaguchi; Toshiyuki Katsube, both of Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 09/444,402

(22) Filed: Nov. 22, 1999

(30) Foreign Application Priority Data

Apr. 20, 1999 (JP) ................................................ 11-112485

(51) Int. Cl.⁷ .......................... C07C 29/76; C07C 29/80; C07C 29/86
(52) U.S. Cl. ......................... 568/842; 534/560; 540/140; 564/271; 568/682
(58) Field of Search ............................ 534/560; 568/682, 568/842; 564/271; 540/140

(56) References Cited

U.S. PATENT DOCUMENTS

| | | | |
|---|---|---|---|
| 2,559,628 | 7/1951 | Joyce, Jr. ............................. | 260/633 |
| 4,970,021 | * 11/1990 | Nakatsuka et al. ............. | 252/299.01 |
| 5,788,914 | * 8/1998 | Oi et al. ............................. | 252/587 |

FOREIGN PATENT DOCUMENTS

| | | |
|---|---|---|
| 294 494 | 10/1991 | (DE) . |
| 2082100 | 12/1971 | (FR) . |

* cited by examiner

*Primary Examiner*—Peter O'Sullivan
(74) *Attorney, Agent, or Firm*—Larson & Taylor PLC

(57) ABSTRACT

In a method for recovering a fluorine-containing solvent from the mixture comprising the fluorine-containing solvent and dyes, (i) a method for recovering a fluorine-containing solvent by distillation; and (ii) a method for recovering a fluorine-containing solvent comprising the steps of adding to the mixture the second solvent which uniformly mixes with the fluorine-containing solvent but does not dissolve the dyes; separating a precipitate from the resulting mixture; and separating the second solvent.

12 Claims, No Drawings

METHOD FOR RECOVERING FLUORINE-CONTAINING SOLVENTS

TECHNICAL FIELD

The present invention relates to a method for recovering fluorine-containing solvents.

BACKGROUND ART

Fluorine-containing solvents are used to dissolve dyes for producing information recording media, for example, CD-R and DVD-R, wherein writable and/or readable recording layers are provided on their substrate by means of a laser. Since fluorine-containing solvents have higher coefficients of global warming than carbon dioxide, it is desirable that the solvents are recovered after use and recycled. However, recovered fluorine-containing solvents have drawbacks for recycle because they contain dyes which are deteriorated or difficult to control their concentrations. It is therefore unfavorable to use the solvents directly after being recovered. Further, if the fluorine-containing solvents are recycled as they are after recovery, it is impossible to change the types of dyes contained therein. Therefore, impurities such as dyes have to be removed from the fluorine-containing solvents to be recycled. However, it has been considered difficult to recover fluorine-containing solvents in a purity enough for producing information recording media such as CD-R because such production requires extremely pure fluorine-containing solvents.

DISCLOSURE OF THE INVENTION

An object of the present invention is to provide a method for recovering a fluorine-containing solvent which is substantially free of impurities.

The inventors of the present invention carried out extensive research on a method for removing dyes from fluorine-containing solvent. The inventors unexpectedly found that the impurities can be readily removed from the solvent by distilling the mixture, thereby recovering a fluorine-containing solvent which is substantially free of dyes and other impurities. In addition, the inventors found that the dyes can be easily separated from the fluorine-containing solvent by adding a specific second solvent to the mixture and a high-purity fluorine-containing solvent can be recovered. The present invention was accomplished based on the above findings.

The present invention provides the processes listed below:
Item 1. A method for recovering a fluorine-containing solvent from a mixture comprising a fluorine-containing solvent and a dye or dyes, wherein the fluorine-containing solvent is recovered by distillation.
Item 2. The method according to item 1, wherein the distillation is conducted under reduced pressure.
Item 3. The method according to item 1, wherein the dye is at least one member selected from the group consisting of cyanine dyes, phthalocyanine dyes, azo dyes, pyrylium dyes, thiopyrylium dyes, squarylium dyes, azulenium dyes, indophenol dyes, indoaniline dyes, triphenylmethane dyes, quinone dyes, aminium dyes, diimmonium dyes and metal complex salt dyes.
Item 4. The method according to item 1, wherein the fluorine-containing solvent is capable of dissolving the dye in 1–10 mass %.
Item 5. The method according to item 1, wherein the fluorine-containing solvent is a fluoroalcohol.
Item 6. The method according to item 5, wherein the fluoroalcohol is represented by the formula (1)

$$H(CFR^1CF_2)_nCH_2OH \tag{1}$$

wherein n=1 or 2; when n=1, $R^1$ represents F or $CF_3$; when n=2, $R^1$ represents F.
Item 7. A method for recovering a fluorine-containing solvent from a mixture comprising a fluorine-containing solvent and a dye or dyes, the method comprising the steps of adding to the mixture a second solvent which are uniformly mixed with the fluorine-containing solvent but does not dissolve the dye; separating a precipitate from the resulting mixture; and separating the second solvent.
Item 8. The method according to item 7, wherein the second solvent is at least one member selected from the group consisting of water, fluoroethers and fluoroalkanes.
Item 9. The method according to item 7, wherein the fluorine-containing solvent is capable of dissolving the dye in 1–10 mass %.
Item 10. The method according to item 7, wherein the fluorine-containing solvent is a fluoroalcohol.
Item 11. The method according to item 10, wherein the fluoroalcohol is represented by the formula (1)

$$H(CFR^1CF_2)_nCH_2OH \tag{1}$$

wherein n=1 or 2; when n=1, $R^1$ represents F or $CF_3$; when n=2, $R^1$ represents F.

The fluorine-containing solvent is not particularly limited insofar as the solvent has at least one fluorine atom. Examples of the preferred fluorine-containing solvents include fluoroalcohols {for example, a fluoroalcohol represented by the formula (1) $H(CFR^1CF_2)_nCH_2OH$ (wherein n=1 or 2; when n=1, $R^1$ represents F or $CF_3$; when n=2, $R^1$ represents F)}; fluorine-substituted ketones ($CF_3COCF_3$, $CF_3COCH_2COCF_3$, $CF_3COCH_2COCH_3$, etc.); fluorine-substituted esters ($CF_3COOCH_3$, $CF_3COOC_2H_5$, $CH_3COOCH_2CF_3$, $CF_3COOCH_2CF_3$, $CH_3COOCH_2CF_2CF_2H$, $CF_3CF_2CF_2CF_2COOC_2H_5$, etc.); fluorinated carboxylic acids {$CF_3(CF_2)_mCOOH$ (m is an integer of 2–4)}, etc.; and fluorinated alkanes ($CCl_2F_2$, $CCl_3F$, $ClF_2C$—$CClF_2$). Among them, the method of the present invention is preferably applied to the recovery of fluoroalcohols, particularly to the recovery of fluoroalcohols represented by the formula (1) $H(CFR^1CF_2)_nCH_2OH$ (n=1 or 2; when n=1, $R^1$ represents F or $CF_3$; when n=2, $R^1$ represents F).

Alternatively, preferably used are fluorine-containing solvents which is capable of dissolving the dyes contained in the mixture in 1–10 mass %.

The dyes contained in the mixture are not particularly limited but include those which are commonly used for producing information recording media comprising a laser-writable and/or a laser-readable recording layer provided on their substrate. Examples of such dyes include cyanine dyes, phthalocyanine dyes, azo dyes, pyrylium dyes, thiopyrylium dyes, squarylium dyes, azulenium dyes, indophenol dyes, indoaniline dyes, triphenylmethane dyes, quinone dyes, aminium dyes, diimmonium dyes and dyes of metal (nickel, copper, cobalt, palladium, platinum, chromium, etc.) complex salt. Specific examples of these dyes are those disclosed in Japanese Examined Patent Publication No. 96333/1995, Japanese Unexamined Patent Publication No. 274732/1997, Japanese Unexamined Patent Publication No. 59529/1997 etc.

Examples of cyanine dyes are $$(CH_2)_2N-(CH=CH)_5-CH=^+N(CH_3)_4ClO_4^-,$$

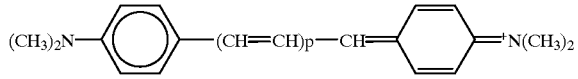

(p=2 or 3) etc.

Examples of phthalocyanine dyes are as follows.

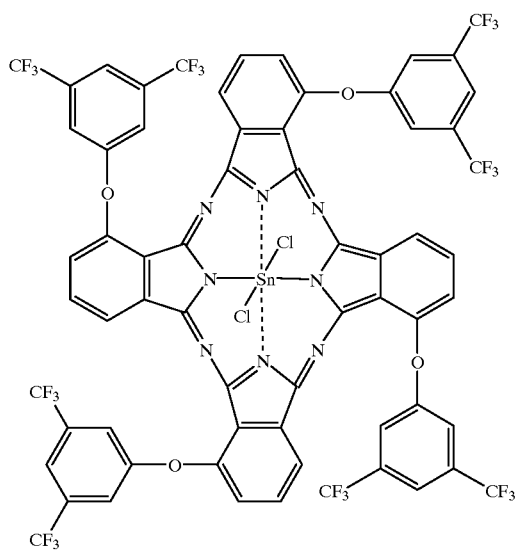

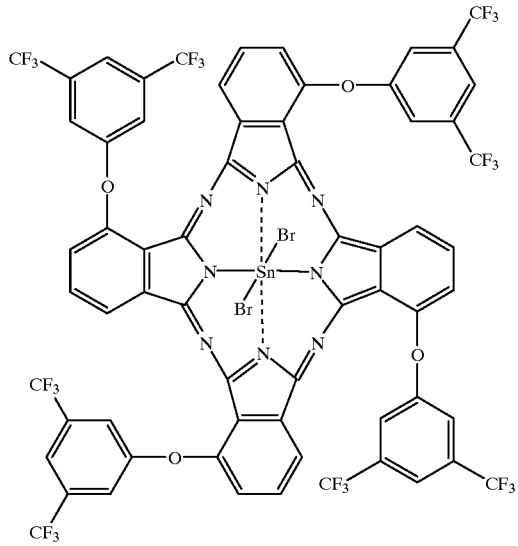

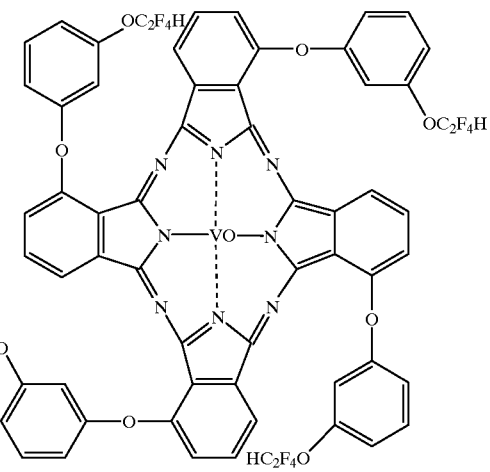

Examples of azo dyes are

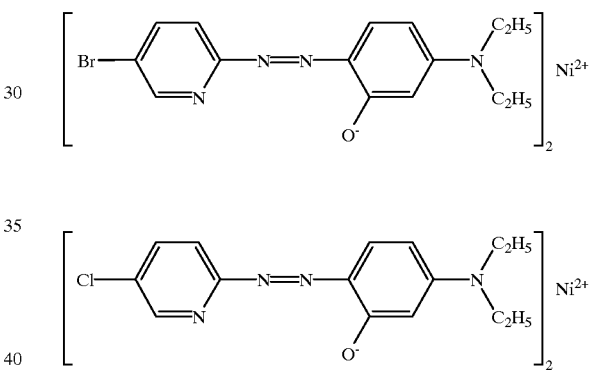

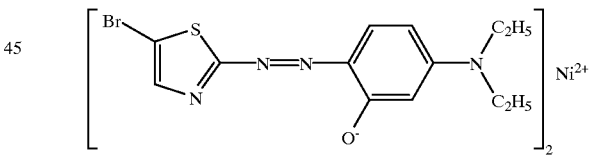

and the like.

Some of these dyes are used for producing information recording media or as quenchers for preventing deterioration or decomposition of other dyes during product storage.

Distillation of the mixture may be carried out usually by heating at a temperature of about 30–150° C. at ambient pressure or under reduced pressure, for example, about 0.0001–0.1 MPa.

When a fluorine-containing solvent is recovered after being used for producing information recording media such as CD-R and DVD-R, the recovered solvent mixture may contain not only dye(s) but also other solvent(s) (e.g., diacetone alcohol) for removing the dye(s) deposited on the periphery of the substrate. Accordingly, when the recovered fluorine-containing solvent mixture contains other solvent or solvents, the recovered solvent mixture is subjected to a fractionation step after removing impurities such as dyes, and to remove other solvent or solvents and to finally obtain the desired fluorine-containing solvent substantially free of impurities. Alternatively, by directly fractionating the recovered solvent mixture, impurities and other solvent(s) are removed simultaneously and the desired fluorine-containing solvent substantially free of impurities can be obtained.

Fractionation may be conducted under suitable conditions depending on the combination of the fluorine-containing solvents and other solvents. For instance, the fractionation may be carried out with heating to about 30–150° C. at ambient pressure or under reduced pressure, for example, about 0.0001–0.1 MPa.

Examples of the second solvents which are uniformly mixed with the fluorine-containing solvent but do not dissolve dyes include water, fluorinated ethers and fluorinated alkanes. The second solvent may be fluorine-containing one which has at least one fluorine atom as far as the solvent differs from the fluorine-containing solvent originally contained in the mixture Examples of the fluorinated ethers include $CF_3CF_2CF_2CF_2OCH_3$, $CF_3CF_2CF_2CF_2OCH_2CH_3$ etc. Examples of fluorinated alkanes include perfluorocyclobutane, $F-(CF_2)_q-F$ (wherein q is integer from 1 to 20) etc.

Preferable combinations of the first solvent (the fluorine-containing solvent originally contained in the mixture) and the second solvent are, for example, a fluoroalcohol and water; a fluoroalcohol and a fluorinated ether; a fluoroalcohol and a fluorinated alkane, etc.

The amount of the second solvent to be added to the mixture is usually about 0.1–10 kg per kilogram of the fluorine-containing solvent (i.e., the first solvent).

When the second solvent is added to the mixture, the dyes are precipitated. The precipitate is separated from the mixture of the fluorine-containing solvent and the second solvent by decantation or like suitable methods. After being separated from the precipitate (i.e., dyes), the mixture is further divided into the fluorine-containing solvent and the second solvent, whereby a fluorine-containing solvent substantially free of impurities is recovered. The separation of the fluorine-containing solvent and the second solvent may be carried out by a suitable method such as distillation, membrane separation, dehydration, pervaporation, etc.

According to the method of the invention, it is possible to recover the fluorine-containing solvent with an evaporation residue of 50 mass ppm or less, preferably 25 mass ppm or less, more preferably 10 mass ppm or less.

The amount of the evaporation residue can be determined as follows. Thus, the fluorine-containing solvent is evaporated at 40° C. under 6.65 hPa (5 mmHg) and the residue is weighed and expressed in mass ppm based on the fluorine-containing solvent.

The UV absorbance in methanol at 205 nm of the fluorine-containing solvent obtained according to the invention is not greater than 0.1 abs, preferably −0.1 abs or less, more preferably −0.2 abs or less. The UV absorbance in methanol can be measured using a mixture of 1 ml of the fluorine-containing solvent and 3 ml of methanol as a sample and methanol as a reference.

That the fluorine-containing solvent obtained by the method of the invention is "substantially free of impurities" means that (i) the residue on evaporation of the fluorine-containing solvent is not more than 50 mass ppm, preferably 25 mass ppm or less, more preferably 10 mass ppm or less and/or (ii) the UV absorbance (at 205 nm) thereof in methanol is not more than 0.1 abs, preferably −0.1 abs or less, more preferably −0.2 abs or less.

According to the present invention, impurities such as dyes, other solvent and decomposition product thereof etc. can be readily separated from a fluorine-containing solvent and a fluorine-containing solvent which is substantially free of impurities can be recovered.

BEST MODE FOR CARRYING OUT THE INVENTION

The present invention is illustrated with the examples given below. It is to be understood that the present invention is not limited to the examples shown herein.

EXAMPLE 1

A solution (500 g) of 10 g of a cyanine dye OM-55 (manufactured by Fuji Photo Film Co., Ltd.), 5 g of a dye IRG-002 (manufactured by Nippon Kayaku Co., Ltd.) used as a quencher and 15 g of diacetone alcohol (DAA) used as detergent of disk such as CD-R in $HCF_2CF_2CH_2OH$ was placed in a glass flask (1 L) equipped with a thermometer, stirrer and vacuum distillation apparatus. The solution was distilled under reduced pressure of 133 hPa (100 mmHg). A distillate (b.p.; 48–60° C.) was collected. The distillate was found to be $HCF_2CF_2CH_2OH$ with a purity of higher than 99.9 mass % and an evaporation residue not more than 10 mass ppm. That is, $HCF_2CF_2CH_2OH$ was substantially free of impurities.

EXAMPLE 2

To the solution (500 g) of the dyes and DAA in $HCF_2CF_2CH_2OH$ used in Example 1 was added 300 g of water. As a result, the dyes were precipitated as a solid. A supernatant separated from the precipitate by decantation was distilled by simple distillation, and a distillate was collected at 80–93° C., in a 631 g quantity of a mixture containing $HCF_2CF_2CH_2OH$: water in a ratio of approximately 7:3 (by weight). The mixture was heated to 70° C. and dehydrated using a pervaporation membrane made of a polyamide resin. As a result, 370 g of $HCF_2CF_2CH_2OH$ with a purity of higher than 99.9 mass % was obtained. The evaporation residue of $HCF_2CF_2CH_2OH$ was not more than 10 mass ppm, that is to say, $HCF_2CF_2CH_2OH$ was substantially free of impurities.

EXAMPLE 3

The procedure of Example 2 was repeated to precipitate the dyes with the exception of using $CF_3CF_2CF_2CF_2OCH_3$ instead of water as the second solvent. A supernatant separated from the precipitate by decantation was distilled by simple distillation. A distillate was collected at 105–110° C. As a result, $HCF_2CF_2CH_2OH$ with a purity of higher than 99.9 mass % and an evaporation residue of not more than 10 mass ppm was obtained. That is, $HCF_2CF_2CH_2OH$ substantially free of impurities was obtained.

EXAMPLE 4

The procedure of Example 2 was repeated to precipitate the dyes with the exception of using $CF_3CF_2CF_2CF_2OCH_2CH_3$ instead of water as the second solvent. A supernatant separated from the precipitate by decantation was distilled by simple distillation. A distillate was collected at 105–110° C., giving $HCF_2CF_2CH_2OH$ with a purity of higher than 99.9 mass % and an evaporation residue of not more than 10 mass ppm. That is, $HCF_2CF_2CH_2OH$ substantially free of impurities was obtained.

EXAMPLE 5

Distillation was conducted following the procedure of Example 1 with the exception of using HCF$_2$CF$_2$CF$_2$CF$_2$CH$_2$OH as the fluorine-containing solvent. A distillate (b.p.; 75–80° C.) was collected, giving HCF$_2$CF$_2$CF$_2$CF$_2$CH$_2$OH distillate with a purity of higher than 99.9 mass %. The evaporation residue of HCF$_2$CF$_2$CF$_2$CF$_2$CH$_2$OH was not more than 10 mass ppm, that is, HCF$_2$CF$_2$CF$_2$CF$_2$CH$_2$OH was substantially free of impurities.

EXAMPLE 6

The procedure of Example 3 was repeated to precipitate the dyes with the exception of using HCF$_2$CF$_2$CF$_2$CF$_2$CH$_2$OH as the fluorine-containing solvent. A supernatant separated from the precipitate by decantation was distilled by simple distillation. A distillate was collected at 135–145° C. As a result, HCF$_2$CF$_2$CF$_2$CF$_2$CH$_2$OH with a purity of higher than 99.9 mass % and an evaporation residue of not more than 10 mass ppm was obtained. That is, HCF$_2$CF$_2$CF$_2$CF$_2$CH$_2$OH substantially free of impurities was obtained.

EXAMPLE 7

Distillation was conducted following the procedure of Example 1 with the exception of using CF$_3$CHFCF$_2$CH$_2$OH as the fluorine-containing solvent. A distillate (b.p.; 50–60° C.) was collected, giving CF$_3$CHFCF$_2$CH$_2$OH with a purity of higher than 99.9 mass % and an evaporation residue of not more than 10 mass ppm. That is, CF$_3$CHFCF$_2$CH$_2$OH was substantially free of impurities.

EXAMPLE 8

The procedure of Example 4 was repeated to precipitate the dyes with the exception of using CF$_3$CHFCF$_2$CH$_2$OH as the fluorine-containing solvent. A supernatant separated from the precipitate by decantation was distilled by simple distillation. A distillate was collected at 110–125° C. As a result, CF$_3$CHFCF$_2$CH$_2$OH with a purity of higher than 99.9 mass % and an evaporation residue of not more than 10 mass ppm was obtained. That is, CF$_3$CHFCF$_2$CH$_2$OH substantially free of impurities was obtained.

What is claimed is:

1. A method for recovering a fluorine-containing solvent from a mixture comprising a fluorine-containing solvent and a dye or dyes, wherein the fluorine-containing solvent is recovered by distillation, the fluorine-containing solvent being a fluoroalcohol.

2. The method according to claim 1, wherein the distillation is conducted under reduced pressure.

3. The method according to claim 1, wherein the dye is at least one member selected from the group consisting of cyanine dyes, phthalocyanine dyes, azo dyes, pyrylium dyes, thiopyrylium dyes, squarylium dyes, azulenium dyes, indophenol dyes, indoaniline dyes, triphenylmethane dyes, quinone dyes, aminium dyes, diimmonium dyes and metal complex salt dyes.

4. The method according to claim 1, wherein the fluorine-containing solvent is capable of dissolving the dye in 1–10 mass %.

5. The method according to claim 1, wherein the fluoroalcohol is represented by the formula (1)

$$H(CFR^1CF_2)_nCH_2OH \tag{1}$$

wherein n=1 or 2; when n=1, R$^1$ represents F or CF$_3$; when n=2, R$^1$ represents F.

6. A method for recovering a fluorine-containing solvent from a mixture comprising a fluorine-containing solvent and a dye or dyes, the method comprising the steps of adding to the mixture a second solvent which is uniformly mixed with the fluorine-containing solvent but does not dissolve the dye; separating a precipitate from the resulting mixture; and separating the second solvent, the fluorine-containing solvent being a fluoroalcohol.

7. The method according to claim 6, wherein the second solvent is at least one member selected from the group consisting of water, fluoroethers and fluoroalkanes.

8. The method according to claim 6, wherein the fluorine-containing solvent is capable of dissolving the dye in 1–10 mass %.

9. The method according to claim 6, wherein the fluoroalcohol is represented by the formula (1)

$$H(CFR^1CF_2)_nCH_2OH \tag{1}$$

wherein n=1 or 2; when n=1, R$^1$ represents F or CF$_3$; when n=2, R$^1$ represents F.

10. The method according to claim 3, wherein the dye is at least one member selected from cyanine dyes.

11. The method according to claim 6, wherein the dye is at least one member selected from cyanine dyes.

12. The method according to claim 6, wherein the second solvent is water.

* * * * *